United States Patent
Bernhard et al.

(10) Patent No.: US 8,602,964 B2
(45) Date of Patent: Dec. 10, 2013

(54) IMPLANTABLE ACTUATOR FOR HEARING AID APPLICATIONS

(75) Inventors: Hans Bernhard, Köniz (CH); Joel Fontannaz, Bulle (CH); Christian Peclat, Neuchatel (CH); Markus Haller, Yens (CH); Karen Cauwels, Kessel-Lo (BE); Ben Kloeck, Edegem (BE); Karel Huybrechts, Kapeele op den Bos (BE); Christof Stieger, Bern (CH); Rudolph Hausler, Celigny (CH); Thomas Kaiser, Borgerhoot (BE)

(73) Assignee: Cochlear Limited, Macquarie University (AU)

( * ) Notice: Subject to any disclaimer, the term of this patent is extended or adjusted under 35 U.S.C. 154(b) by 850 days.

(21) Appl. No.: 11/719,975

(22) PCT Filed: Nov. 30, 2005

(86) PCT No.: PCT/AU2005/001801
§ 371 (c)(1),
(2), (4) Date: Mar. 25, 2008

(87) PCT Pub. No.: WO2006/058368
PCT Pub. Date: Jun. 8, 2006

(65) Prior Publication Data
US 2008/0188707 A1    Aug. 7, 2008

Related U.S. Application Data

(60) Provisional application No. 60/631,512, filed on Nov. 30, 2004.

(51) Int. Cl.
*H04R 25/00* (2006.01)
(52) U.S. Cl.
USPC .......................................................... 600/25

(58) Field of Classification Search
USPC ................ 600/25; 181/130; 381/326; 607/57
See application file for complete search history.

(56) References Cited

U.S. PATENT DOCUMENTS 4,756,312 A * 7/1988 Epley ............................... 607/57
4,913,155 A * 4/1990 Dow et al. ..................... 600/446
(Continued)

FOREIGN PATENT DOCUMENTS

WO    WO 95/01710 A1    1/1995

OTHER PUBLICATIONS

International Search Report. PCT/AU2005/001801. Feb. 6, 2006.
(Continued)

*Primary Examiner* — Christine Matthews
(74) *Attorney, Agent, or Firm* — Lowe, Hauptman & Ham

(57) ABSTRACT

An electromechanical actuator (100) suitable, for example, in hearing aid applications is disclosed. Certain embodiments of the actuator comprise a hermetic titanium housing (1), a mechanical output structure (110) emulating the long process of incus (8), and means for efficiently generating movement in the audible frequency range. The electromechanical actuator (100) may be configured to be coupled to the inner ear fluids via a conventional stapes prosthesis. The implantable actuator (100), which may be considered to be operably equivalent to a loudspeaker of a conventional hearing aid, may bypass the outer and the middle ear in order to directly drive the inner ear fluids. As such, embodiments of the electromechanical actuator of the present invention may be used to remedy any source of conductive hearing loss. Additionally, certain embodiments of the electromechanical actuator may be configured to provide sufficiently high output levels to treat severe sensorineural hearing loss while being sufficiently small to completely fit into a human mastoid.

8 Claims, 7 Drawing Sheets

(56) References Cited

U.S. PATENT DOCUMENTS

| | | | |
|---|---|---|---|
| 5,277,694 | A | 1/1994 | Leysieffer et al. |
| 6,162,169 | A | 12/2000 | Leysieffer |
| 6,554,762 | B2 | 4/2003 | Leysieffer |
| 2004/0097785 | A1 | 5/2004 | Schmid et al. |

OTHER PUBLICATIONS

Australian Examiner's Report dated Mar. 17, 2009.

* cited by examiner

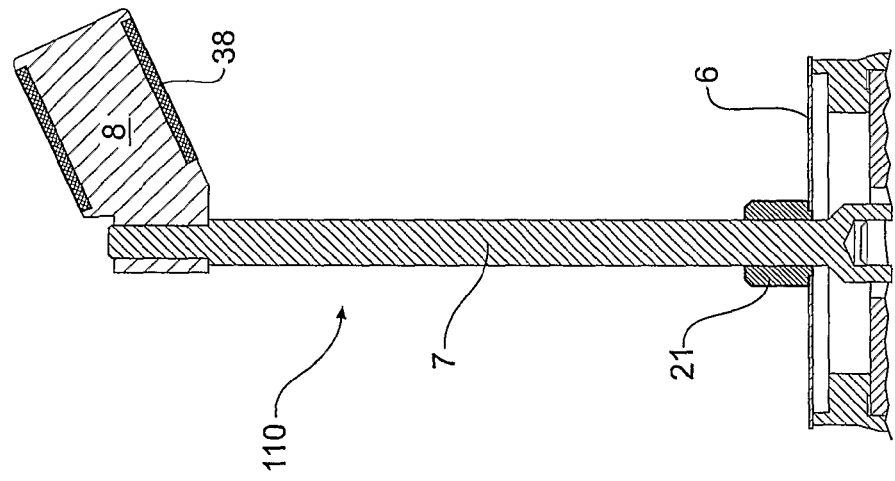
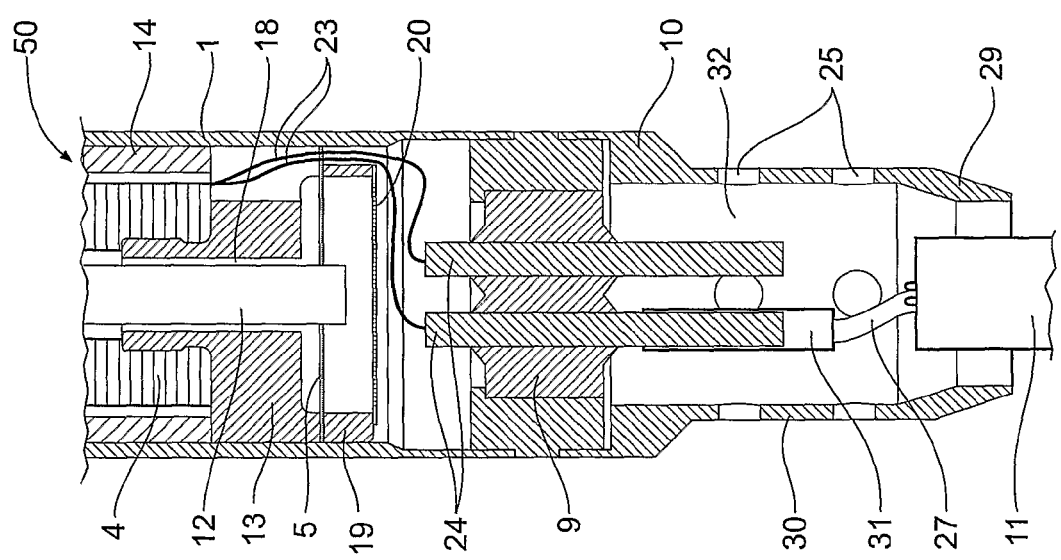

IMPLANTABLE ACTUATOR FOR HEARING AID APPLICATIONS

RELATED APPLICATIONS

The present application is a national stage application under 35 USC 0371(c) of PCT Application No. PCT/AU2005/001801, entitled "Implantable Actuator For Hearing Aid Applications," filed on Nov. 30, 2005, which claims the priority of U.S. Provisional Patent Application No. 60/631,512 entitled "Implantable Fixation System for Anchorage of Medical Devices' filed 30 Nov. 2004, which is hereby incorporated by reference herein in its entirety.

FIELD OF THE INVENTION

The present invention relates to treatments for hearing loss. In a particular form, the present invention relates to an implantable actuator capable of direct stimulation of the middle and inner ear auditory systems.

BACKGROUND OF THE INVENTION

Today state-of-the-art conventional hearing aids are able to treat hearing loss, in particular sensorineural hearing loss, very efficiently but still have some major disadvantages such as occlusion of the auditory canal, feedback at high amplification levels and stigmatization of the patients with hearing loss. Further they are rather ineffective in the treatment of conductive and mixed hearing loss. Whilst the present invention is described in relation to the treatment of hearing loss it will be appreciated that the invention will have other applications consistent with the principles described in the specification.

It is an object of the present invention to provide a stimulation device capable of being included in an implantable hearing aid device that addresses one or more of the disadvantages of conventional hearing aid devices.

SUMMARY OF THE INVENTION

In a first aspect the present invention accordingly provides an electromechanical actuator comprising:
  first and second magnets arranged to provide a biasing field in a field region between two substantially opposed pole faces of said first and second magnets;
  a magnetically permeable armature located in said biased field region between said opposed pole faces, the location of the magnetically permeable armature defining a first and second working gap between the magnetically permeable armature and respective opposed pole faces of the first and second magnets;
  a magnetically permeable armature shaft assembly supporting said magnetically permeable armature, said magnetically permeable armature shaft assembly arranged to allow movement of said magnetically permeable armature between said opposed pole faces in a longitudinal direction defined by the movement of said armature shaft assembly;
  biasing means for providing a biasing force to said magnetically permeable armature shaft assembly to bias said magnetically permeable armature to a predetermined location between said opposed pole faces; and
  magnetic flux generating means responsive to an input signal to generate a signal flux to modulate said biasing field in said field region thereby providing an unbalanced force to said magnetically permeable armature causing actuation of said magnetically permeable armature shaft assembly.

Preferably, said first and second magnets are supported by a magnet support assembly and wherein said magnet support assembly, said magnetically permeable armature and said first and second working gaps form a first magnetic circuit.

Preferably, said magnetic flux generating means is supported by a flux generating means support assembly and wherein said flux generating means support assembly, said magnetically permeable armature, said magnetically permeable armature shaft assembly and one of said first and second working gaps forms a second magnetic circuit.

Preferably, said magnetic flux generating means comprises an electrical coil.

Preferably, said flux generating means support assembly comprises a magnetically permeable structure having a recess to receive a shaft of said magnetically permeable armature shaft assembly, thereby forming a transverse air gap between said shaft and the walls of said recess.

Preferably, said recess is substantially cylindrical in shape.

Preferably, said transverse air gap is minimized to reduce the reluctance of said second magnetic circuit.

Preferably, said biasing means includes a first biasing member and a second biasing member.

Preferably, said flux generating means support assembly comprises said first biasing member and wherein said first biasing member further comprises a magnetically permeable spring in mechanical contact with a shaft of said magnetically permeable armature shaft assembly.

Preferably, said second biasing member comprises a diaphragm in mechanical contact with said shaft.

In a second aspect the present invention accordingly provides an electromechanical actuator for an implantable hearing aid device comprising:
  a hermetic housing of tubular shape closed on one side with a diaphragm and on the other side, with a hermetic feedthrough;
  first and second magnets located in said hermetic housing arranged to provide a biasing field in a field region between two substantially opposed pole faces of said first and second magnets;
  a magnetically permeable armature located in said biased field region between said opposed pole faces, the location of the magnetically permeable armature defining a first and second working gap between the magnetically permeable armature and respective opposed pole faces of the first and second magnets;
  a magnetically permeable armature shaft assembly supporting said magnetically permeable armature, said magnetically permeable armature shaft assembly arranged to allow movement of said magnetically permeable armature between said opposed pole faces in a longitudinal direction defined by the movement of said magnetically permeable armature shaft assembly;
  biasing means to provide a biasing force to said magnetically permeable armature shaft assembly to bias said magnetically permeable armature to a predetermined location between said opposed pole faces;
  magnetic flux generating means including an electrical signal coil responsive to an input signal delivered by an electrical connection to said hermetic feedthrough to generate a signal flux to modulate the biasing field in said field region thereby providing an unbalanced force to said magnetically permeable armature causing actuation of said magnetically permeable armature shaft assembly;

a mechanical output structure including stimulation means to stimulate the inner ear auditory system responsive to actuation of said magnetically permeable armature shaft assembly; and a lead electrically connected to outer pins of said hermetic feedthrough and mechanically attached to said titanium housing.

In a third aspect the present invention accordingly provides an implantable stimulation device for stimulating an inner ear of a patient, said stimulation device including an electromechanical actuator responsive to an auditory signal for providing mechanical stimulation to said inner ear in response to said auditory signal.

Preferably, said stimulation device further includes a middle ear prosthetic, said middle ear prosthetic reproducing in part or in full the function of the middle ear, wherein said electromechanical actuator includes actuation means to actuate said middle ear prosthetic thereby stimulating said inner ear in response to said auditory signal.

BRIEF DESCRIPTION OF THE DRAWINGS

A preferred embodiment of the present invention will be discussed with reference to the accompanying drawings wherein:

FIG. 5 is a lower elevation view in longitudinal diametric section of the electromechanical actuator illustrated in FIG. 1, showing the attachment of coil wires and lead;

FIG. 6 is an elevation view in longitudinal diametric section of the electromechanical actuator illustrated in FIG. 1, showing the mechanical output structure;

In the following description, like reference characters designate like or corresponding parts throughout the several views of the drawings.

DESCRIPTION OF PREFERRED EMBODIMENT

Figure 1:
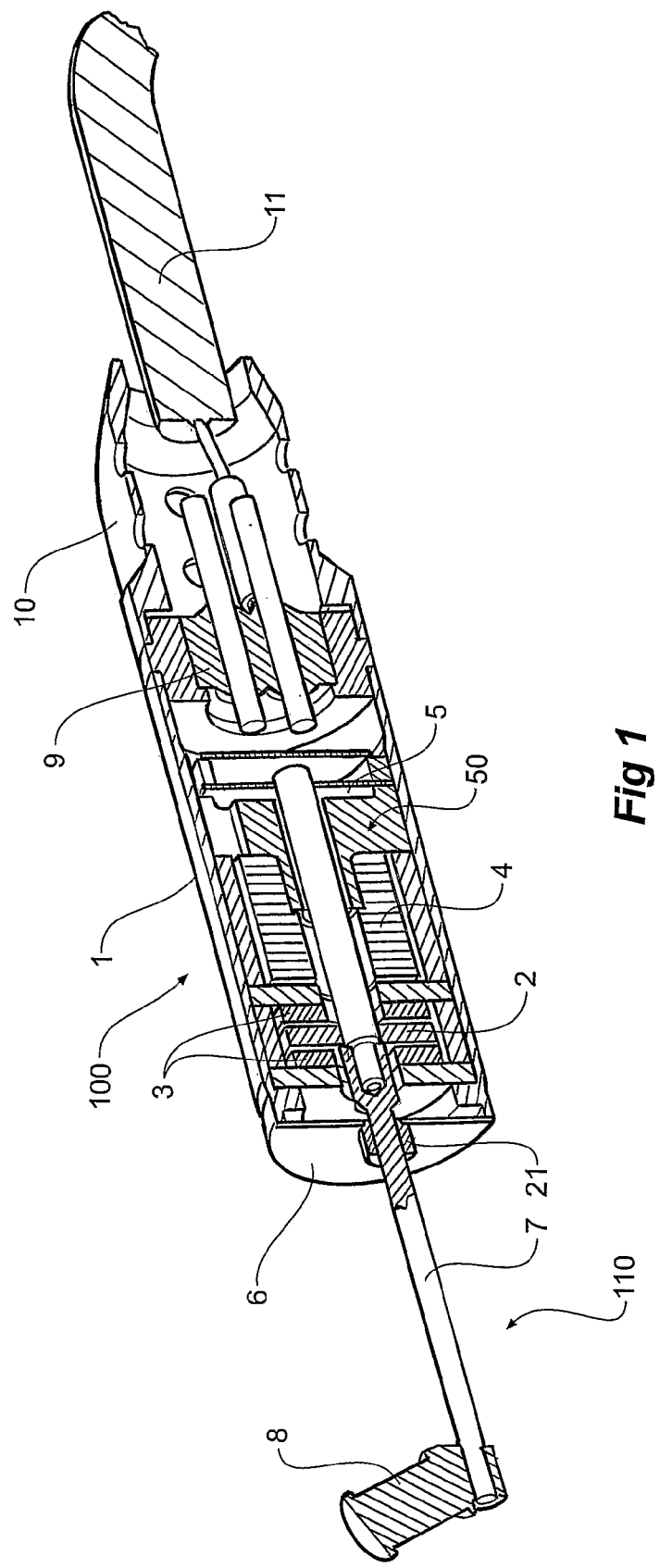
FIG. 1 is a perspective view of the interior components of an implantable hearing aid device incorporating an electromechanical actuator in accordance with a first embodiment of the present invention.
Figure 2:
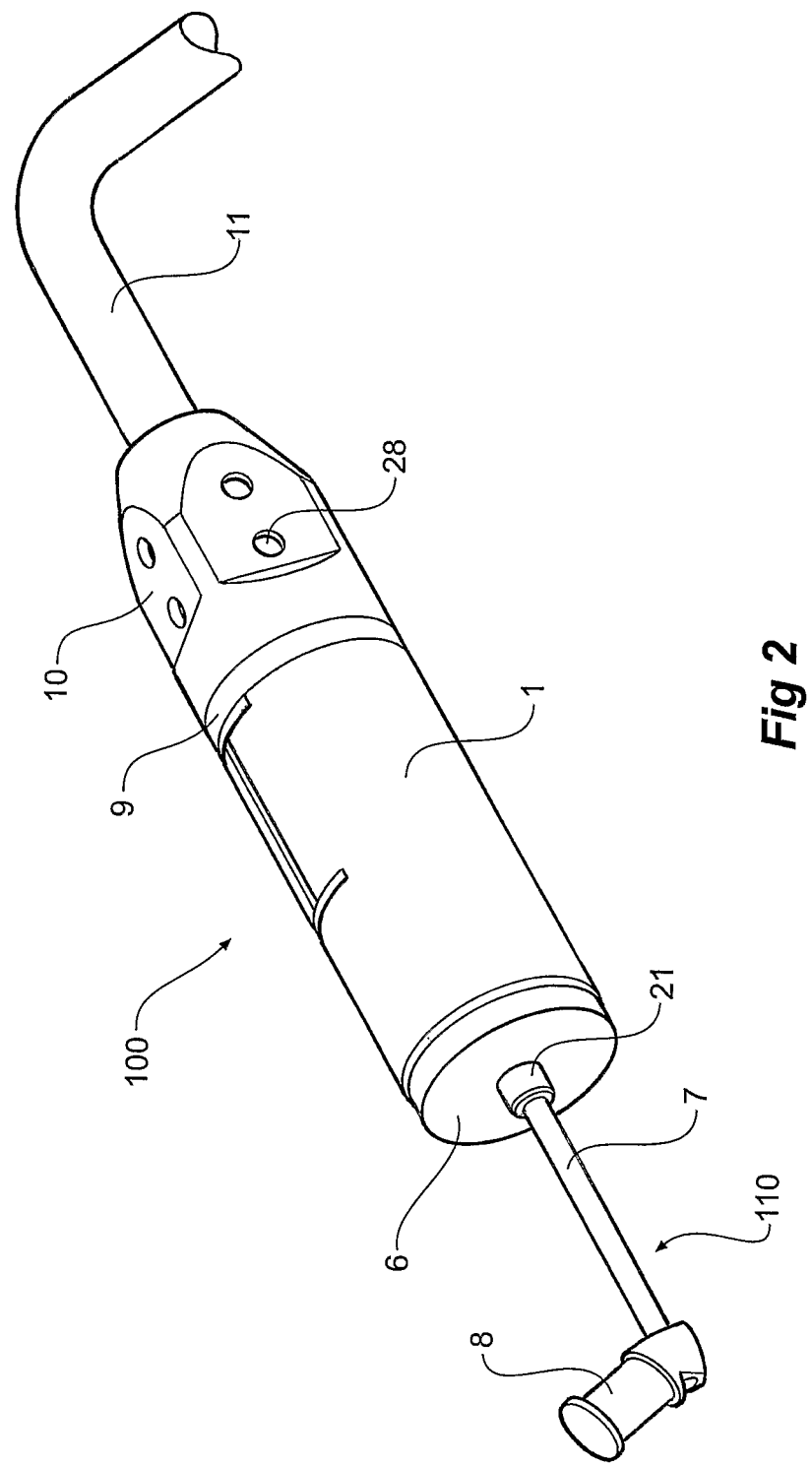
FIG. 2 is a composite view of the implantable hearing aid device illustrated in FIG. 1.

Referring now to FIGS. 1 and 2, there are shown perspective and composite views depicting the components of an implantable hearing aid device 100 incorporating an electromechanical actuator 50 according to a first embodiment of the present invention. Hearing aid device 100 includes a housing 1 formed from titanium tubing that is substantially cylindrical and of circular cross section. Hearing aid device 100 further comprises a titanium diaphragm 6, a titanium ring 21 and a multi-pin feedthrough 9 which are joined by hermetic laser welds. Coupling rod 7, which is part of the moving mechanical output structure of electromechanical actuator 50, is placed in ring 21 and is hermetically welded to it. This assembly provides a hermetically closed housing 1 that is suitable for implantation in the human body.

Lead 11 which provides the input signal to electromechanical actuator 50 is connected to feedthrough 9. To protect the connection site of the lead 11, electromechanical actuator 50 may be covered by a silicone filled titanium cap 10. In this embodiment directed to a hearing aid device, the titanium cap 10 provides multiple flat surface regions to allow secure manipulation of the device during implantation with surgical tweezers or little tongs. The titanium cap 10 also has a conical shape that provides mechanical transition between the small diameter of the lead 11 and larger diameter of the titanium tube 1.

Figure 3:
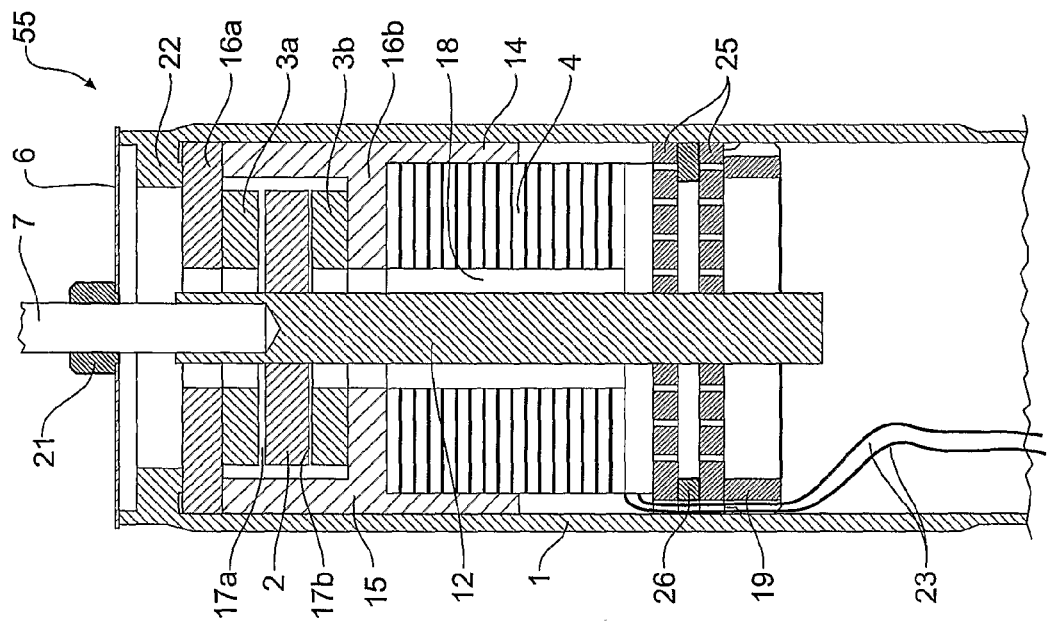
FIG. 3 is an elevation view in longitudinal diametric section of the electromechanical actuator illustrated in FIG. 1 having a low reluctance transverse gap.

Referring now to FIG. 3, there is shown an elevation view in longitudinal diametric section of the first embodiment of electromechanical actuator 50 of the present invention incorporating a low reluctance transverse gap. Armature 2, shaft 12 and coupling rod 7 form the moving part of the actuator 50. As armature 2 and shaft 12 form part of the magnetic circuits which drive electromechanical actuator 50 they are made of soft magnetic alloys. However, as would be understood by those skilled in the art, other suitable materials having the desired magnetic permeability properties may also be used.

Shaft 12 is made of titanium to enable hermetic closing of the actuator by welding it to a ring 21. The resulting moving structure is elastically supported at one side by a diaphragm 6, which performs the function of a restoring spring. As such, diaphragm 6 prevents magnetic snap over. On the other side, shaft 12 is supported in the longitudinal direction by a spring bearing 5 having a spring constant sufficient to provoke, together with diaphragm 6, the demanded dynamic characteristic of this spring-mass structure.

The armature 2 is centered between two permanent magnets 3a and 3b thereby forming two working gaps 17a and 17b. Both magnets 3a and 3b are polarized in the same direction substantially in parallel to the actuator axis and the direction of movement of shaft 12, and provide polarizing flux in working gaps 17a and 17b that extends through the armature 2. This first magnetic circuit is closed through the magnet supports 16a and 16b and the short sleeve 15 which are again fabricated from soft magnetic alloys.

A second magnetic circuit comprises signal coil 4, coil core 13, long sleeve 14, the magnet support 16b, the armature 2 and the shaft 12. Signal coil 4 includes two input coil wires 23 which are connected to lead 11 by virtue of feedthrough 9. Preferably, all elements forming the second magnetic circuit other than the signal coil 4 are made of soft magnetic alloys to conduct the signal flux generated by coil 4. This magnetic signal circuit includes two air gaps: the working gap 17b and a transverse gap 18 formed between the coil core 13 and the shaft 12. The transverse gap 18 between the coil core 13 and shaft 12 has been minimized in order to provide a low reluctance thereby minimize losses in the magnetic circuit.

In operation, the signal flux passing through the working gap 17b has the effect of modulating the polarizing flux generated by the magnets 3a and 3b in the process either increasing or decreasing the flux in the working gap 17b depending on the direction of the current passing through the signal coil 4. This in turn increases or decreases the attractive force in gap 17b compared to the constant polarizing flux in gap 17a which results in a net force pulling the armature upwards or downwards. In this manner, small changes in the signal flux generated by coil 4 will result in corresponding actuation of shaft 12 thereby providing an electromechanical actuator of enhanced sensitivity.

Figure 4:
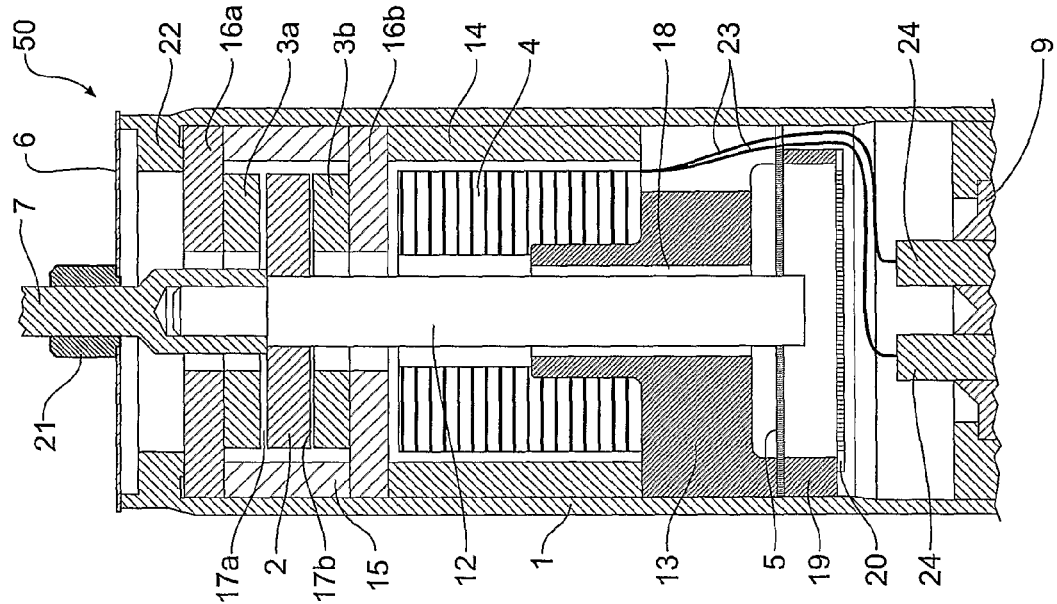
FIG. 4 is an elevation view in longitudinal diametric section of a second embodiment of an electromechanical actuator of the present invention having a flux conducting spring member.

Referring now to FIG. 4, there is shown an elevation view in longitudinal diametric section of a second embodiment of an electromechanical actuator 55. The main structure of the electromechanical actuator 55 is the same as shown in FIG. 3, however, the spring bearing 5 and the transverse gap 18 of the FIG. 3 embodiment are replaced by flux conducting spring members 25 in this second embodiment. Flux conducting spring members 25 are preferably made of soft magnetic alloys providing reduced reluctance to overcome the losses resulting from the increased air gap 18 when compared to the air gap between the shaft 12 and coil core 13 in the first embodiment.

The use of multiple spring members 25 separated by flux conducting spacers 26 increases the sectional area that can be passed by the magnetic flux to further reduce the overall reluctance of the magnetic circuit. Compared to one spring that is simply increased in thickness, the multiple springs provide higher compliance.

Referring now to FIG. 5, there is shown an elevation view in longitudinal diametric section of the first embodiment of the electromechanical actuator 55 showing the attachment of the coil wires 23 and lead 11. Coil wires 23 are attached to feedthrough pins 24 by, for example, brazing, welding or gluing with an electrically conductive glue. To prevent coil wires 23 from coming into contact with moving shaft 12 or spring bearing 5, a cover 20 is placed between the coil wires and the shaft.

The terminals 27 of lead 11 are inserted in a crimping tube 31 that is welded to the feedthrough pin 24. Crimping the tube 31 mechanically attaches lead terminal 27 and establishes a low-impedance electrical connection. In this embodiment, a cap 10 protects the whole connection site. The cavity 32 formed by the cap 10 is filled up with silicone to provide a firm mechanical attachment of the lead 11. To enable proper sterilization of the silicone, the cap 10 provides multiple openings 28.

Referring now to FIG. 6, there is shown an elevation view in longitudinal diametric section of the moving mechanical output structure 110 forming part of the implantable hearing aid device 100 illustrated in FIGS. 1 and 2. Mechanical output structure 110 comprises a coupling rod 7 and an artificial incus 8, both made of titanium and, in this embodiment, welded together. A silicone coating 38 covers artificial incus 8. The artificial incus 8 closely emulates the long process of the incus of the human middle ear, and is placed next to it during implantation.

The length of the coupling rod 7, measured from the outer surface of the diaphragm 6 to the end of the coupling rod 7, is chosen in the range from approximately 3 mm to approximately 20 mm, and preferably in the range from approximately 5 mm to approximately 8 mm, to place the artificial incus 8 in the intended location. The angle formed by the axis of the coupling rod 7 and the axis of the artificial incus 8 is chosen in the range from 80° to 150°, preferably in the range from 115° to 125°, in order to correctly orientate the artificial incus 8 according to the anatomical conditions in the human middle ear.

The cross sectional profile of the artificial incus 8 is elliptical with a numeric eccentricity in the range from 0 to 0.5 in order to provide reliable mechanical connection of the stapes prosthesis by crimping. Additionally, the artificial incus 8 is covered with a silicone coating 38 that has a thickness chosen in the range from 0.05 mm to 0.2 mm in order to allow proper stapes prosthesis attachment and crimping. It should be appreciated that the above dimensions and distances are approximate and that other dimensions may be established in alternative embodiments.

Figure 7:
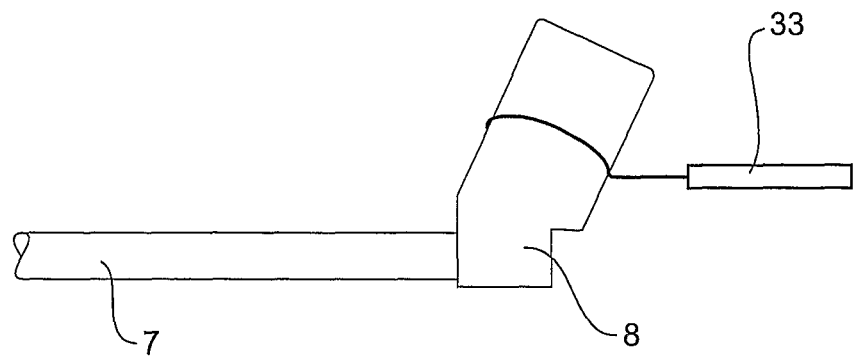
FIG. 7 is a side view of the mechanical output structure illustrated in the above figures, with an attached stapes prosthesis.

Referring now to FIG. 7, there is shown a schematic diagram of one embodiment of the mechanical output structure of FIG. 6 with an attached stapes prosthesis 33.

Figure 8:
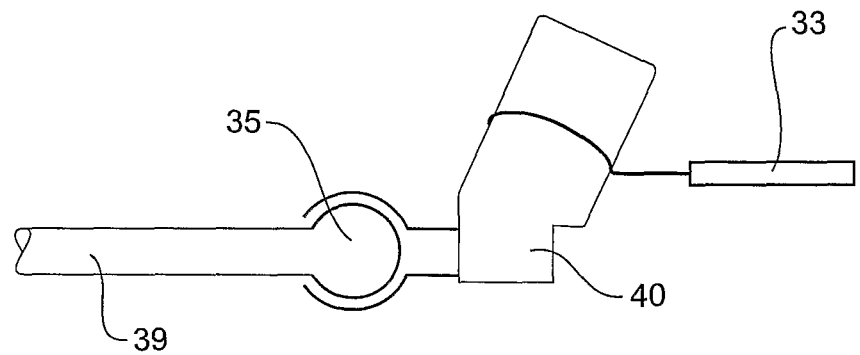
FIG. 8 is a side view of the mechanical output structure illustrated in the above figures, having a ball joint between coupling rod and artificial incus.

Referring now to FIG. 8, there is shown another embodiment of the mechanical output structure having a ball joint 35 between coupling rod 39 and artificial incus 40 to allow intra-operative adjustment of the angle between the coupling rod 39 and the artificial incus 40.

Figure 9:
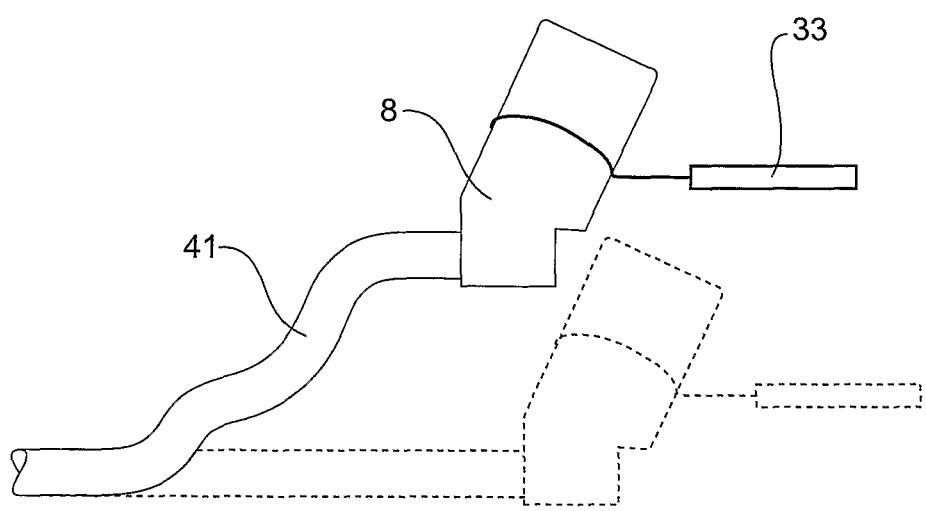
FIG. 9 is a side view of the mechanical output structure illustrated in the above figures, having a bendable coupling rod.
Figure 10:
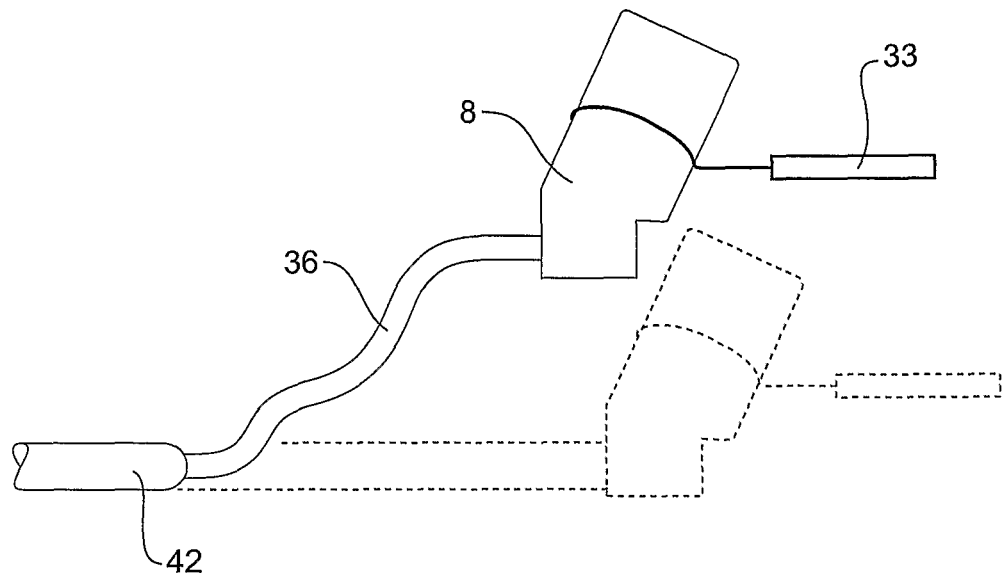
FIG. 10 is a side view of the mechanical output structure illustrated in the above figures, having a partially bendable coupling rod.

Referring now to FIG. 9, there is shown yet another embodiment of the mechanical output structure having a bendable coupling rod 41 to allow intra-operative adjustment of the orientation and the location of the artificial incus 8. FIG. 10 shows yet another embodiment of the mechanical output structure having a two part coupling rod, a stiff part 42 next to actuator 50, 55 and a bendable part 36 next to the artificial incus 8 to allow intra-operative adjustment of the orientation and the location of the artificial incus 8.

Figure 11:
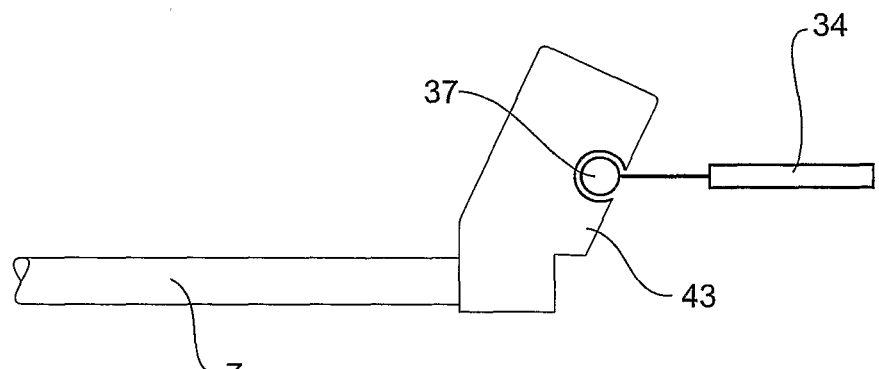
FIG. 11 is a side view of the mechanical output structure illustrated in the above figures, having a ball joint between artificial incus and stapes prosthesis.

Referring now to FIG. 11, there is shown a further embodiment of the mechanical output structure having a stapes prosthesis 34 directly attached to the artificial incus 43 via a ball joint 37 to allow intra-operative adjustment of the insertion angle of the stapes prosthesis 34.

Figure 12:
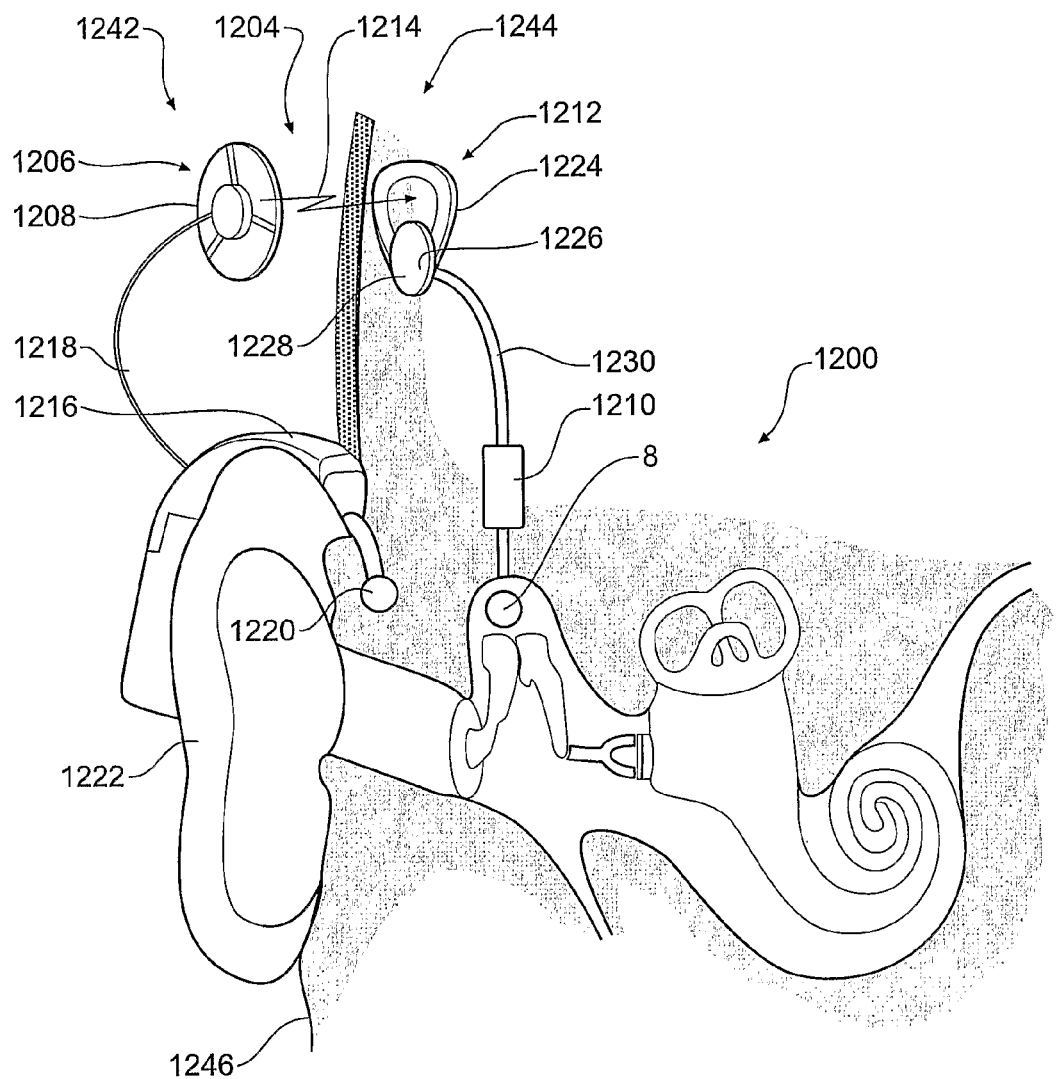
FIG. 12 is a perspective view of a cochlear implant system showing one exemplary application of the electromechanical actuator of the present invention.

Referring now to FIG. 12, there is shown implantable hearing aid device 1200 implementing an electromechanical actuator 1210 according to a preferred embodiment of the present invention. In this preferred embodiment, implantable hearing aid device 1200 is a totally implantable Cochlear™ prosthesis (also referred to as a Cochlear™ implant system, Cochlear™ prosthetic device and the like) which functions as an implantable stimulation device for stimulating the inner ear by employing an electromechanical actuator responsive to an auditory signal. As would be apparent to those skilled in the art, the electromechanical actuator of the present invention can be utilized in current or future implantable medical devices. These implantable medical devices can be either partially or totally implanted in an individual, and such implantation may be temporary or permanent.

Hearing aid device 1200 comprises external component assembly 1242 which is directly or indirectly attached to the body of the recipient, and an internal component assembly 1244 which is temporarily or permanently implanted in the recipient. External assembly 1242 typically comprises audio pickup devices 1220 for detecting sound, a speech processing unit 1216, a power source (not shown), and an external transmitter unit 1206 comprising an external coil 1208. Speech processing unit 1216 processes the output of audio pickup devices 1220 that are positioned by the ear 1222 of the recipient. Speech processing unit 1216 generates coded signals which are provided to external transmitter unit 1206 via cable 1218.

Internal components 1244 comprise an internal receiver unit 1212, a stimulator unit 1226, and a moving electromechanical actuator 1210 according to a preferred embodiment of the present invention. Internal receiver unit 1212, which comprises an internal transcutaneous transfer coil 1224, and stimulator unit 1226 are hermetically sealed within a housing 1228. Collectively, transmitter antenna coil 1208 and receiver antenna coil 1224 form an inductively-coupled coil system used to transfer data and power via a radio frequency (RF) link 114. A cable 1230 extends from stimulator unit 1226 to actuator 1210.

Actuator 1210 is coupled to the inner ear fluids via artificial incus 8 extending through a cochleostomy. Signals generated by stimulator unit 1226 are applied by mechanical actuator 1210 to inner ear fluids. It should be appreciated that the arrangement shown in FIG. 12 is a schematic representation only, and that embodiments of the electromechanical actuator 1210 of the present invention may be positioned in a variety of locations to provide the desired stimulative effect. For example, in the embodiment shown in FIG. 12, actuator 1210 is coupled to the inner ear fluids via artificial incus 8. However, a variety of stapes prostheses may be attached to artificial incus 8 in alternative embodiments, as described above.

It should also be appreciated that electromechanical actuator 1210 may be secured to the recipient utilizing a variety of techniques now or later developed. In one embodiment, electromechanical actuator 1210 is configured to be implanted in a recipient utilizing an embodiment of a fixation system described in commonly owned U.S. Provisional Patent Application No. 60/631,512 entitled "Implantable Fixation System for Anchorage of Medical Devices," filed 30 Nov. 2004, which is hereby incorporated by reference herein in its entirety.

A brief consideration of the above described embodiments will indicate that the invention may be employed to remedy any source of conductive hearing loss. Additionally, these embodiments of the electromechanical actuator may be configured to provide sufficiently high output levels to treat severe sensorineural hearing loss while being sufficiently small to completely fit into a human mastoid.

It should also be appreciated that Cochlear™ implant system 1200 described above is just one exemplary system in which the electromechanical actuator of the present invention may be implemented. The electromechanical actuator of the present invention may be implemented in a myriad of embodiments of a cochlear implant system, hearing aid or other medical devices or systems now or later developed.

Advantageously, the dimensions and shape of embodiments of the electromechanical actuator of the present invention may be selected to take into account the anatomy of the implantation site. For example, for an actuator that is to be placed in a hole drilled into the human mastoid, an elongated cylindrical shape such as that described above has been found to be advantageous. In addition, in the above or other application, embodiments of the actuator may have a diameter and a length which are sufficiently small to allow placement of the actuator in narrow anatomical locations as required. A further advantage of embodiments of the present invention directed to hearing aid devices is that they are able to deliver sufficiently high output levels to manage progressive hearing loss in order to prevent revision surgeries. A still further advantage is that certain embodiments of the actuator are highly energy efficient thereby minimizing power consumption and facilitating autonomy.

Although a preferred embodiment of the method and system of the present invention has been described in the foregoing detailed description, it will be understood that the invention is not limited to the embodiment disclosed, but is capable of numerous rearrangements, modifications and substitutions without departing from the scope of the invention as set forth and defined by the following claims.

It will be understood that the term "comprise" and any of its derivatives (eg. comprises, comprising) as used in this specification is to be taken to be inclusive of features to which it refers, and is not meant to exclude the presence of any additional features unless otherwise stated or implied.

The invention claimed is:

1. An electromechanical actuator comprising:
   first and second magnets arranged to provide a biasing field in a field region between two substantially opposed pole faces of said first and second magnets, said opposed pole faces facing in a longitudinal direction of the actuator;
   a magnetically permeable armature located in said biasing field region between said opposed pole faces, the location of the magnetically permeable armature defining a first and second working gap between the magnetically permeable armature and said opposed pole faces of the first and second magnets;
   a magnetically permeable armature shaft assembly extending in said longitudinal direction of the actuator and supporting said magnetically permeable armature, said magnetically permeable armature shaft assembly arranged to allow movement of said magnetically permeable armature between said opposed pole faces in said longitudinal direction;
   biasing means for providing a biasing force to said magnetically permeable armature shaft assembly to bias said magnetically permeable armature to a predetermined location between said opposed pole faces; and
   magnetic flux generating means responsive to an input signal to generate a signal flux to modulate said biasing field in said field region thereby providing an unbalanced force to said magnetically permeable armature causing actuation of said magnetically permeable armature shaft assembly,
   wherein said opposed pole faces of the first and second magnets are oriented facing toward each other in said longitudinal direction.

2. The electromechanical actuator as claimed in claim 1, wherein said first and second magnets are supported by a magnet support assembly and wherein said magnet support assembly, said magnetically permeable armature and said first and second working gaps form a first magnetic circuit.

3. The electromechanical actuator as claimed in claim 2, wherein said magnetic flux generating means is supported by a flux generating means support assembly and wherein said flux generating means support assembly, said magnetically permeable armature, said magnetically permeable armature shaft assembly and one of said first and second working gaps forms a second magnetic circuit.

4. The electromechanical actuator as claimed in claim 3, wherein said flux generating means support assembly comprises a magnetically permeable structure having a recess to receive a shaft of said magnetically permeable armature shaft assembly, thereby forming a transverse air gap between said shaft and walls of said recess.

5. The electromechanical actuator as claimed in claim 4, wherein said recess is substantially cylindrical in shape.

6. The electromechanical actuator as claimed in claim 4, wherein said transverse air gap is minimized to reduce reluctance of said second magnetic circuit.

7. An electromechanical actuator comprising:
   first and second magnets arranged to provide a biasing field in a field region between two substantially opposed pole faces of said first and second magnets;
   a magnetically permeable armature located in said biasing field region between said opposed pole faces, the location of the magnetically permeable armature defining a first and second working gap between the magnetically permeable armature and respective opposed pole faces of the first and second magnets;

a magnetically permeable armature shaft assembly supporting said magnetically permeable armature, said magnetically permeable armature shaft assembly arranged to allow movement of said magnetically permeable armature between said opposed pole faces in a longitudinal direction defined by the movement of said armature shaft assembly;

biasing means for providing a biasing force to said magnetically permeable armature shaft assembly to bias said magnetically permeable armature to a predetermined location between said opposed pole faces; and magnetic flux generating means responsive to an input signal to generate a signal flux to modulate said biasing field in said field region thereby providing an unbalanced force to said magnetically permeable armature causing actuation of said magnetically permeable armature shaft assembly, wherein said magnetic flux generating means comprises an electrical coil which is fixed relative to the first and second magnets, wherein said biasing means includes a first biasing member and a second biasing member and wherein said flux generating means is supported by a flux generating means support assembly that comprises said first biasing member and said first biasing member further comprises a magnetically permeable spring in mechanical contact with a shaft of said magnetically permeable armature shaft assembly.

8. The electromechanical actuator as claimed in claim 7, wherein said second biasing member comprises a diaphragm in mechanical contact with said shaft.

* * * * *